United States Patent
Wu et al.

(10) Patent No.: US 8,419,808 B2
(45) Date of Patent: *Apr. 16, 2013

(54) DYE COMPOUND AND PHOTOELECTRIC COMPONENT USING THE SAME

(75) Inventors: Ming-si Wu, Taoyuan Hsien (TW); Wei-Cheng Tang, Taoyuan Hsien (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,321

(22) Filed: Nov. 2, 2011

(65) Prior Publication Data

US 2012/0042457 A1 Feb. 23, 2012

Related U.S. Application Data

(62) Division of application No. 12/320,232, filed on Jan. 22, 2009, now Pat. No. 8,203,068.

(30) Foreign Application Priority Data

Nov. 14, 2008 (CN) .......................... 2008 1 0173497

(51) Int. Cl.
*H01L 31/04* (2006.01)
*C09B 67/10* (2006.01)

(52) U.S. Cl.
USPC ............... 8/550; 8/552; 8/568; 8/572; 8/573; 540/1; 549/1

(58) Field of Classification Search .............. 8/550, 552, 8/568, 572, 573; 540/1; 549/1
See application file for complete search history.

(56) References Cited

U.S. PATENT DOCUMENTS

| | | | |
|---|---|---|---|
| 7,569,704 B1 | 8/2009 | Lin et al. | |
| 2006/0130249 A1 | 6/2006 | Ikeda et al. | |
| 2007/0073052 A1* | 3/2007 | Velusamy et al. | 540/1 |
| 2007/0240756 A1 | 10/2007 | Lee et al. | |
| 2008/0067476 A1 | 3/2008 | Shigaki et al. | |
| 2008/0149175 A1 | 6/2008 | Horiuchi et al. | |
| 2009/0044857 A1 | 2/2009 | Shigaki et al. | |
| 2010/0122729 A1 | 5/2010 | Wu et al. | |
| 2011/0100462 A1 | 5/2011 | Tang et al. | |
| 2012/0042457 A1 | 2/2012 | Wu et al. | |

FOREIGN PATENT DOCUMENTS

| | | |
|---|---|---|
| EP | 1981118 A1 | 10/2008 |
| JP | 2006-156213 | 6/2006 |

OTHER PUBLICATIONS

Kuang et al., "Organic Dye-Sensitized Ionic Liquid Based Solar Cells: Remarkable Enhancement in Performance through Molecular Design of Indoline Sensitizers", Angew. Chem. Int. Ed, 2008, vol. 47, pp. 1923-1927.

Horiuchi et al., "High Efficiency of Dye-Sensitized Solar Cells Based on Metal-Free Indoline Dyes", J. Am. Chem. Soc., 2004, vol. 126, pp. 12218-12219.

Yen et al., "Pyrrole-Based Organic Dyes for Dye-Sensitized Solar Cells", J. Phys. Chem. C, 2008, vol. 112, pp. 12557-12567.

Scifinder Search Strategy, American Chemical Society, Apr. 17, 2012, pp. 1-9.

Lee et al., "Effects of co-adsorbate and additive on the performance of dye-sensitized solar cells: A photophysical study", Solar Energy Materials & Solar Cells, 2007, vol. 91, pp. 1426-1431.

\* cited by examiner

*Primary Examiner* — Brian P Mruk

(74) *Attorney, Agent, or Firm* — Bacon & Thomas PLLC

(57) ABSTRACT

The present invention relates to a dye compound represented by the following formula (I), or a salt thereof:

(I)

wherein $R_1$, $R_2$, $R_3$, $R_4$, $D_1$, $D_2$, B, and n are defined the same as the specification, and also relates to a photoelectric component using the same. The dye compound of the present invention is suitable for Dye-Sensitized Solar Cell (DSSC). Hence, the photoelectric characteristics of the DSSC can be improved by using the dye compound of the present invention.

12 Claims, No Drawings

DYE COMPOUND AND PHOTOELECTRIC COMPONENT USING THE SAME

This application is a divisional application of U.S. patent application Ser. No. 12/320,232, filed Jan. 22, 2009, which has issued as U.S. Pat. No. 8,203,068 (of which the entire disclosure of the pending, prior application is hereby incorporated by reference).

BACKGROUND OF THE INVENTION

1. Field of the Invention

The present invention relates to a dye compound and a photoelectric component using the same and, more particularly, to a dye compound, which is used for the dye-sensitized solar cell (DSSC), and a photoelectric component using the same.

2. Description of Related Art

With the development of industrial technology, the serious problems that the whole world is facing today are the energy crisis and the environmental pollution. In order to solve the global energy crisis and to reduce the environmental pollution, one of the effective means is the solar cell, which can convert the solar energy into the electricity. Since the dye-sensitized solar cell has the advantages of low manufacturing cost, large-scale production, great flexibility, light transmittance, and being capable of use in the buildings, the application of the dye-sensitized solar cell becomes more and more attractive.

Currently, Grätzel et al. have disclosed a series of literatures, for example, O'Regan, B.; Grätzel, M. *Nature* 1991, 353, 737, which shows the practicability of the dye-sensitized solar cell. The general structure of the dye-sensitized solar cell comprises an anode, a cathode, a nano-porous titanium dioxide layer, a dye, and electrolyte, wherein the dye plays a critical role in the conversion efficiency of the dye-sensitized solar cell. The dye suitable for the dye-sensitized solar cell must have characteristics in broad absorption spectrum, high molar absorption coefficient, thermal stability, and light stability.

The ruthenium complexes are the sensitized dyes with the higher conversion efficiency nowadays. However, the manufacturing cost of the ruthenium complexes is high, and there may be problems of short supply when the ruthenium complexes are used widely. The organic sensitizers for the dye-sensitized solar cell have advantages of high molar absorption coefficient. Besides, it is possible to produce various organic sensitizers through molecular design. Hence, dye-sensitized solar cells with different colors can be manufactured to improve the application flexibility of the dye-sensitized solar cells. In addition, it is also possible to change the color of the dye-sensitized solar cell to match with the color of objects. Currently, dye derivatives, such as coumarin (Hara, K.; Sayama, K.; Arakawa, H.; Ohga, Y.; Shinpo, A.; Sug, S. *Chem. Commun.* 2001, 569), indoline (Horiuchi, T.; Miura, H.; Sumioka, K.; Uchida, S. *J. Am. Chem. Soc.* 2004, 126, 12218), and merocyanine (Otaka, H.; Kira, M.; Yano, K.; Ito, S.; Mitekura, H.; Kawata, T.; Matsui, F. *J Photochem. Photobiol. A: Chem.* 2004, 164, 67), have already applied in the manufacture of dye-sensitized solar cells.

However, the process for synthesis of sensitized dyes is very complicated, and it is difficult to control the synthesis condition of sensitized dyes.

The dyes for the dye-sensitized solar cell influence the conversion efficiency critically. Hence, it is desirable to provide a dye compound, which can improve the conversion efficiency of the dye-sensitized solar cell. In addition, it is also important to simplify the method for synthesis of dye compounds, in order to reduce the cost of manufacturing dye-sensitized solar cells.

SUMMARY OF THE INVENTION

The object of the present invention is to provide a novel dye compound, which is suitable for a dye-sensitized solar cell. In addition, the dye compound of the present invention has high molar absorption coefficient, so that it is possible to improve the photoelectric conversion efficiency of a dye-sensitized solar cell by the dye compound of the present invention.

Another object of the present invention is to provide a simple method for synthesis of a dye compound, wherein the synthesis steps of the dye compound is less, the process is easy to control, and the cost of synthesis is lower.

Furthermore, another object of the present invention is to provide a dye-sensitized solar cell, which shows higher photoelectric conversion efficiency.

Hence, the present invention provides a dye compound represented by the following formula (I), or a salt thereof:

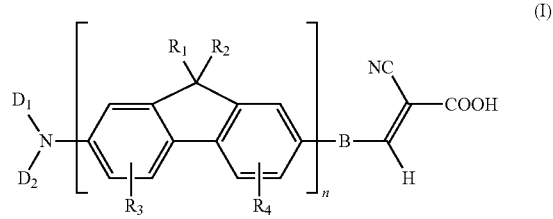

wherein,
$R_1$, $R_2$, $R_3$, and $R_4$ are each independently H, $C_1$~$C_{12}$ alkyl, $C_1$~$C_{12}$ alkoxy, or a halogen, and n is 1, 2, or 3;
$D_1$, and $D_2$ are each independently $C_1$~$C_{12}$ alkyl,

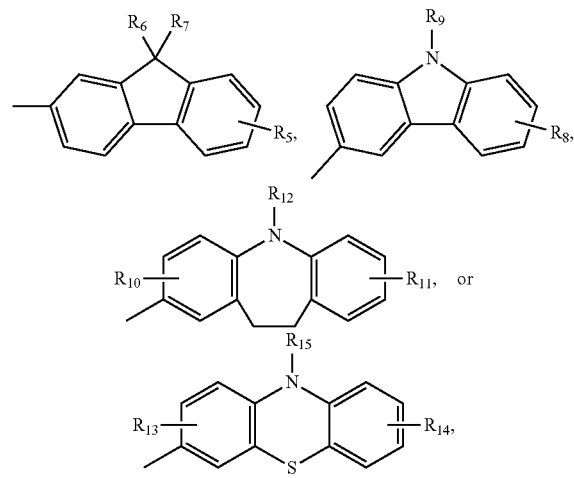

or $D_1$, $D_2$, and N bond together to form

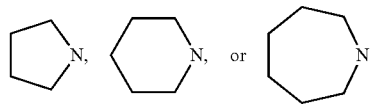

(i.e. $C_4$~$C_6$ cycloheteroalkylene), wherein $R_5$, $R_6$, $R_7$, $R_8$, $R_{10}$, $R_{11}$, $R_{13}$, and $R_{14}$ are each independently H, $C_1$~$C_{12}$ alkyl, $C_1$~$C_{12}$ alkoxy, amino, or halogen, and $R_9$, $R_{12}$, and $R_{15}$ are each independently H, or $C_1$~$C_{12}$ alkyl;

B is

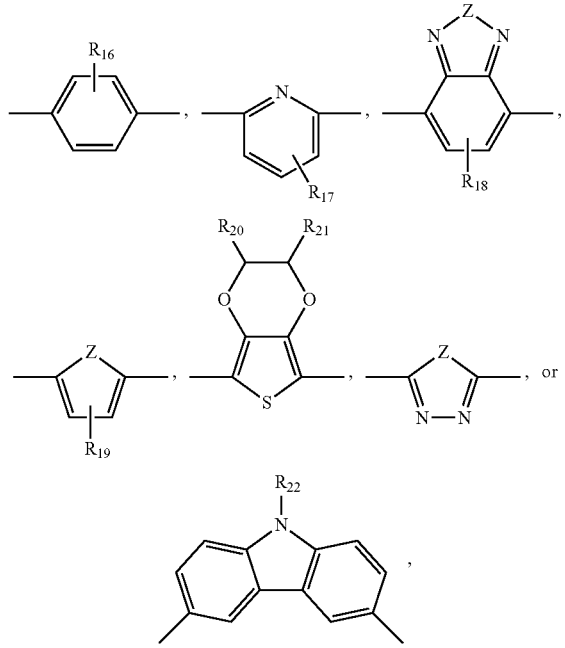

wherein $R_{16}$, $R_{17}$, and $R_{18}$ are each independently H, $C_1$~$C_{12}$ alkyl, $C_1$~$C_{12}$ alkoxy, or halogen, $R_{19}$, $R_{20}$, $R_{21}$, and $R_{22}$ are each independently H, or $C_1$~$C_{12}$ alkyl, and Z is O, S, or Se.

In the above formula (I), $R_1$, $R_2$, $R_3$, and $R_4$ are each independently H, $C_1$~$C_{12}$ alkyl, $C_1$~$C_{12}$ alkoxy, or halogen, and n is 1, 2, or 3. Preferably, $R_1$, $R_2$, $R_3$, and $R_4$ are each independently H, $C_1$~$C_{12}$ alkyl, $C_1$~$C_{12}$ alkoxy, or halogen, and n is 1, or 2. More preferably, $R_1$, $R_2$, $R_3$, and $R_4$ are each independently H, $C_1$~$C_{12}$ alkyl, or $C_1$~$C_{12}$ alkoxy, and n is 1, or 2. Still more preferably, $R_1$, $R_2$, $R_3$, and $R_4$ are each independently H, $C_1$~$C_{12}$ alkyl, or $C_1$~$C_{12}$ alkoxy, and n is 1. Mort preferably, $R_1$, $R_2$, $R_3$, and $R_4$ are each independently H, or $C_1$~$C_{12}$ alkyl, and n is 1.

In the above formula (I), $D_1$, and $D_2$ are each independently $C_1$~$C_{12}$ alkyl,

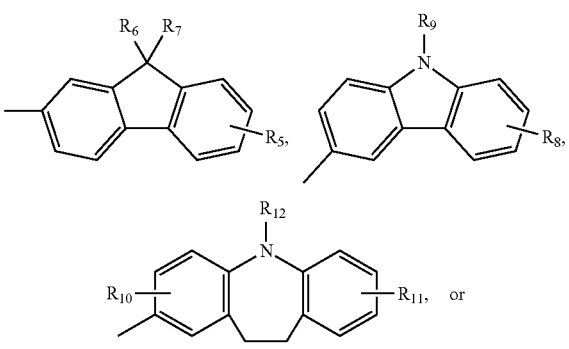

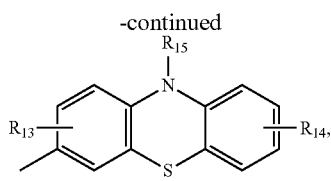

or $D_1$, $D_2$, and N bond together to form

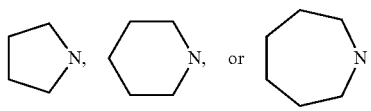

(i.e. $C_4$~$C_6$ cycloheteroalkylene), wherein $R_5$, $R_6$, $R_7$, $R_8$, $R_{10}$, $R_{11}$, $R_{13}$, and $R_{14}$ are each independently H, $C_1$~$C_{12}$ alkyl, $C_1$~$C_{12}$ alkoxy, amino, or halogen, and $R_9$, $R_{12}$, and $R_{15}$ are each independently H, or $C_1$~$C_{12}$ alkyl. Preferably, $D_1$, and $D_2$ are each independently $C_1$~$C_{12}$ alkyl,

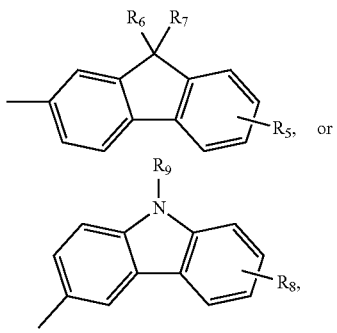

wherein $R_5$, $R_6$, $R_7$, and $R_8$ are each independently H, $C_1$~$C_{12}$ alkyl, $C_1$~$C_{12}$ alkoxy, amino, or halogen, and $R_9$, is H, or $C_1$~$C_{12}$ alkyl. More preferably, $D_1$, and $D_2$ are each independently $C_1$~$C_{12}$ alkyl,

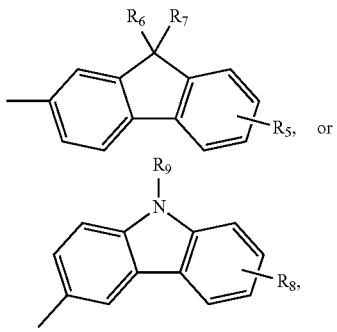

wherein $R_5$, $R_6$, $R_7$, and $R_8$ are each independently H, $C_1$~$C_{12}$ alkyl, or $C_1$~$C_{12}$ alkoxy, and $R_9$, is H, or $C_1$~$C_{12}$ alkyl. Most preferably, $D_1$, and $D_2$ are each independently $C_1$~$C_{12}$ alkyl,

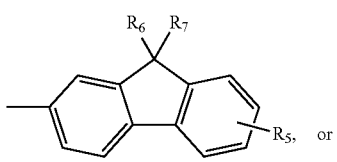

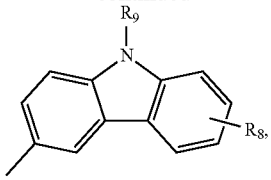

wherein $R_5$, $R_6$, $R_7$, $R_8$, and $R_9$ are each independently H, or $C_1$~$C_{12}$ alkyl.

In addition, according to one embodiment of the present invention, in the above formula (I), $D_1$, and $D_2$ are each independently $C_1$~$C_{12}$ alkyl, or

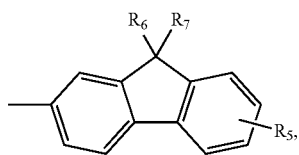

wherein $R_5$, $R_6$, and $R_7$ are each independently H, $C_1$~$C_{12}$ alkyl, $C_1$~$C_{12}$ alkoxy, amino, or halogen. Preferably, in $D_1$, and $D_2$, $R_5$, $R_6$, and $R_7$ are each independently H, $C_1$~$C_{12}$ alkyl, or $C_1$~$C_{12}$ alkoxy. Most preferably, in $D_1$, and $D_2$, $R_5$, $R_6$, and $R_7$ are each independently H, or $C_1$~$C_{12}$ alkyl.

In the above formula (I), B may be

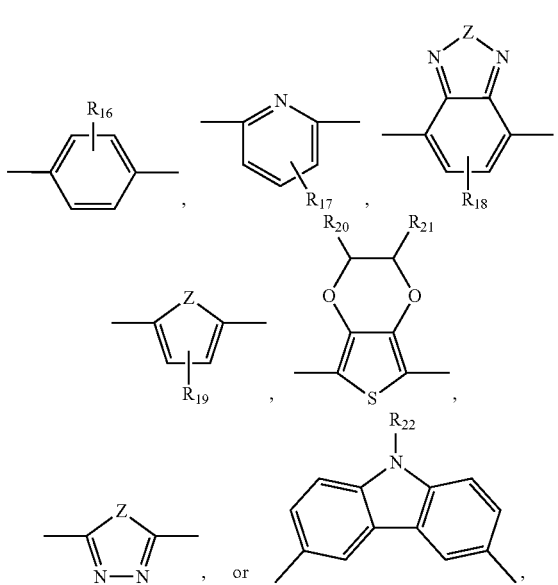

wherein $R_{16}$, $R_{17}$, and $R_{18}$ are each independently H, $C_1$~$C_{12}$ alkyl, $C_1$~$C_{12}$ alkoxy, or halogen, $R_{19}$, $R_{20}$, $R_{21}$, and $R_{22}$ are each independently H, or $C_1$~$C_{12}$ alkyl, and Z is O, S, or Se. Preferably, B is

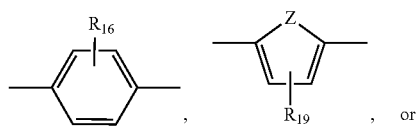

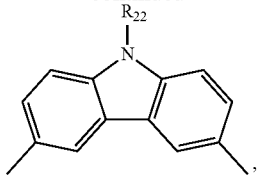

wherein $R_{16}$ is H, $C_1$~$C_{12}$ alkyl, $C_1$~$C_{12}$ alkoxy, or halogen, $R_{19}$, and $R_{22}$ are each independently H, or $C_1$~$C_{12}$ alkyl, and Z is O, S, or Se. More preferably, B is

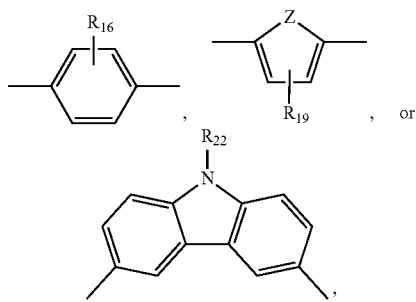

wherein $R_{16}$ is H, $C_1$~$C_{12}$ alkyl, $C_1$~$C_{12}$ alkoxy, or halogen, $R_{19}$, and $R_{22}$ are each independently H, or $C_1$~$C_{12}$ alkyl, and Z is S. Most preferably, B is

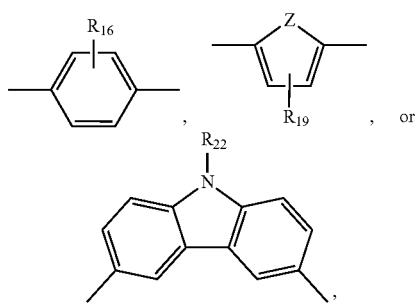

wherein $R_{16}$, $R_{19}$, and $R_{22}$ are each independently H, or $C_1$~$C_{12}$ alkyl, and Z is S.

In addition, according to one embodiment of the present invention, in the above formula (I), B may be

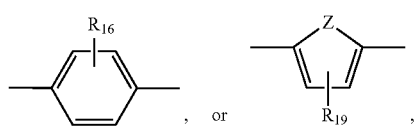

wherein $R_{16}$ is H, $C_1$~$C_{12}$ alkyl, $C_1$~$C_{12}$ alkoxy, or halogen, $R_{19}$ is H, or $C_1$~$C_{12}$ alkyl, and Z is O, S, or Se. Preferably, B is

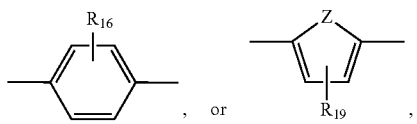, or wherein $R_{16}$ is H, $C_1$~$C_{12}$ alkyl, $C_1$~$C_{12}$ alkoxy, or halogen, $R_{19}$ is H, or $C_1$~$C_{12}$ alkyl, and Z is S. More preferably, B is

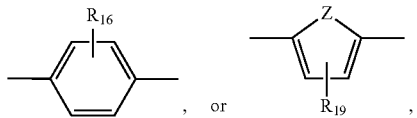, or wherein $R_{16}$ is H, $C_1$~$C_{12}$ alkyl, or $C_1$~$C_{12}$ alkoxy, $R_{19}$ is H, or $C_1$~$C_{12}$ alkyl, and Z is S. Still more preferably, B is

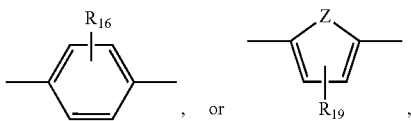, or wherein $R_{16}$ and $R_{19}$ are each independently H, or $C_1$~$C_{12}$ alkyl, and Z is S. Most preferably, B is

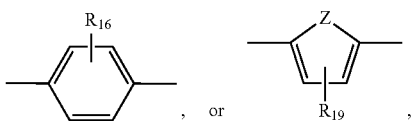, or wherein $R_{16}$ and $R_{19}$ are H, and Z is S.

The specific examples of the dye compound represented by the above formula (I) are:

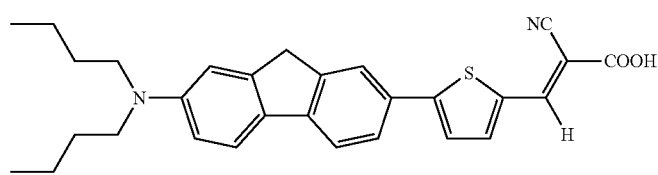

(13a)

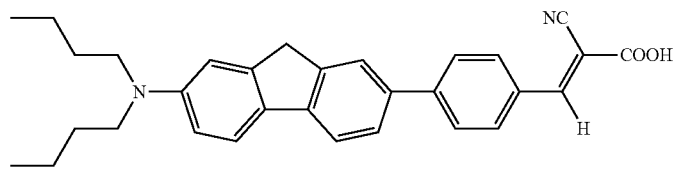

(13b)

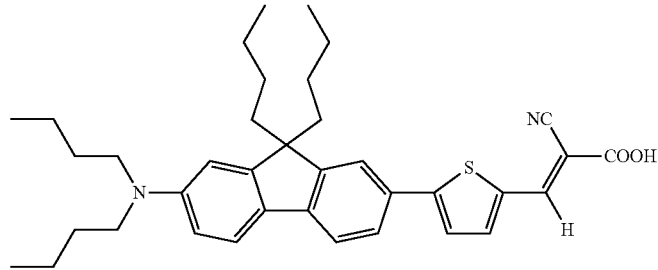

(23a)

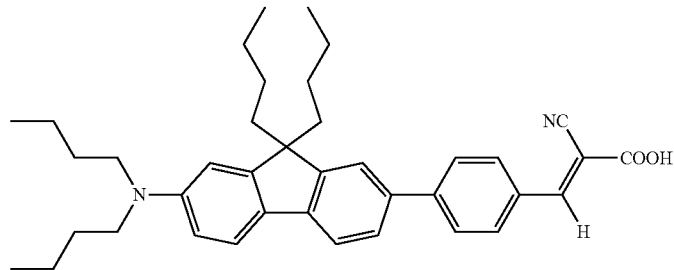

(23b)

-continued

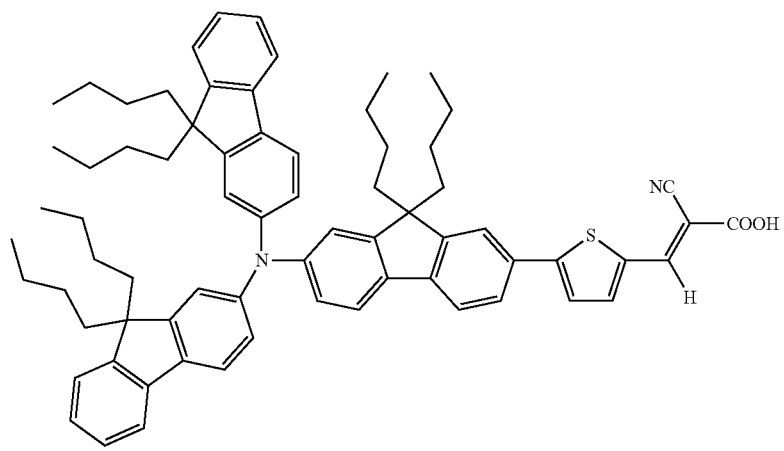

(35a)

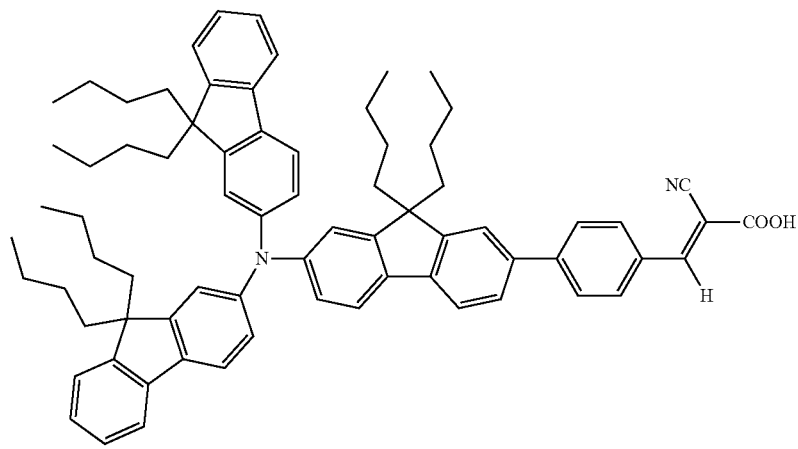

(35b)

In the present invention, the molecule of the dye compound is presented in form of free acid. However, the actual form of the dye compound of the present invention may be salt, and more likely, may be alkaline metal salt or quaternary ammonium salt.

In addition, the aforementioned dye compound is used as a dye compound for a dye-sensitized solar cell.

Furthermore, the present invention also provides a dye-sensitized solar cell, which comprises the aforementioned dye compound. The dye-sensitized solar cell of the present invention comprises: a photoanode comprising the aforementioned dye compound; a cathode; and an electrolyte layer disposed between the photoanode and the cathode.

In the dye-sensitized solar cell of the present invention, the photoanode comprises: a transparent substrate, a transparent conductive layer, a porous semiconductive layer, and a dye compound; wherein the dye compound is the aforementioned dye compound.

In the dye-sensitized solar cell of the present invention, the material of the transparent substrate is not particularly limited, as long as the material of the substrate is a transparent material. Preferably, the material of the transparent substrate has good moisture resistance, solvent resistance and weather resistance. Thus, the dye-sensitized solar cell can resist moisture or gas from outsides by the transparent substrate. The specific examples of the transparent substrate include, but are not limited to, transparent inorganic substrates, such as quartz and glass; transparent plastic substrates, such as poly(ethylene terephthalate) (PET), poly(ethylene 2,6-naphthalate) (PEN), polycarbonate (PC), polyethylene (PE), polypropylene (PP), and polyimide (PI). Additionally, the thickness of the transparent substrate is not particularly limited, and can be modified according to the transmittance and the demands for the properties of the dye-sensitized solar cell. Preferably, the material of the transparent substrate is glass.

Furthermore, in the dye-sensitized solar cell of the present invention, the material of the transparent conductive layer can be indium tin oxide (ITO), fluorine-doped tin oxide (FTO), $ZnO\text{—}Ga_2O_3$, $ZnO\text{—}Al_2O_3$, or tin-based oxides.

In addition, in the dye-sensitized solar cell of the present invention, the porous semiconductive layer is made of semiconductor particles. Suitable semiconductor particles may include Si, $TiO_2$, $SnO_2$, ZnO, $WO_3$, $Nb_2O_5$, $TiSrO_3$, and the combination thereof. Preferably, the semiconductor particles are made from $TiO_2$. The average diameter of the semiconductor particles may be 5 to 500 nm. Preferably, the average diameter of the semiconductor particles is 10 to 50 nm. Furthermore, the thickness of the porous semiconductive layer is 5-25 μm.

Besides, the material of the cathode for the dye-sensitized solar cell is not particularly limited, and may include any material with conductivity. Otherwise, the material of the cathode can be an insulating material, as long as there is a conductive layer formed on the surface of the cathode, wherein the surface of the cathode is faced to the photoanode. The material of the cathode can be any material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes.

On the other hand, the present invention further provides a dye solution, which comprises: (A) the aforementioned dye compound, wherein the content of the dye compound is 0.01-1 wt %; and (B) an organic solvent, wherein the content of the organic solvent is 99.99-99 wt %, and the organic solvent is selected from the group consisting of acetonitrile, methanol, ethanol, propanol, butanol, dimethyl formamide, and N-methyl-2-pyrrolidinone.

Other objects, advantages, and novel features of the invention will become more apparent from the following detailed description when taken in conjunction with the accompanying drawings.

DETAILED DESCRIPTION OF THE PREFERRED EMBODIMENT

The dye compound of the present invention can be synthesised by Schemes 1 to 3.

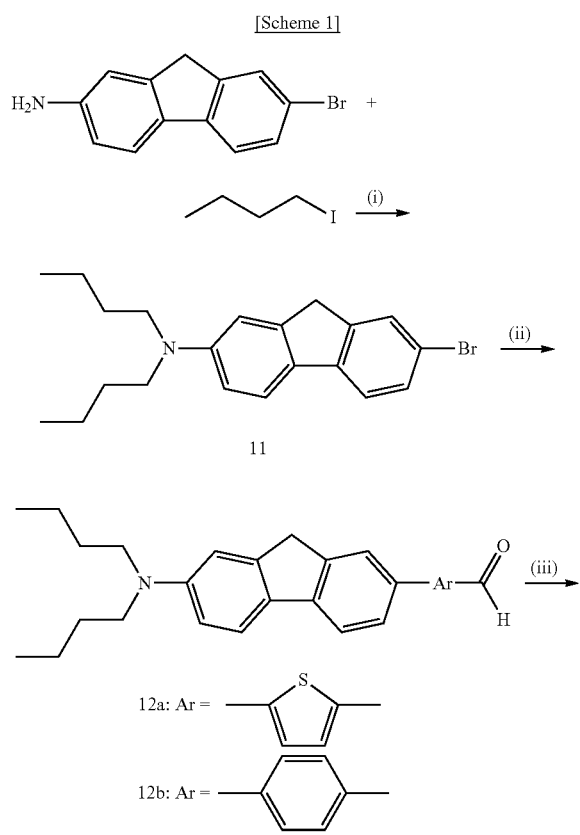

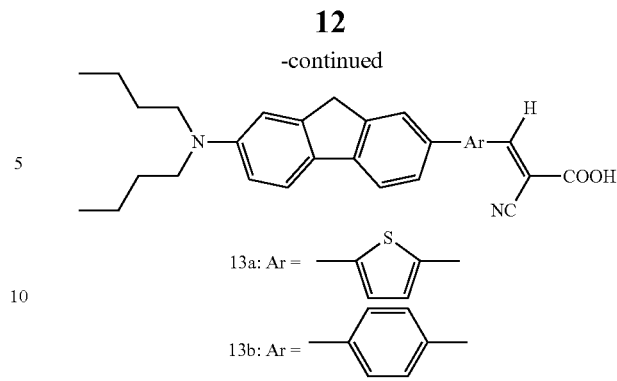

(i) $K_2CO_3$, DMF.
(ii) $PdCl_2$(dppf), 5-formyl-2-thiopheneboronic acid or 4-formylphenylboronic acid, $K_2CO_3$, $CH_2OH$/toluene.
(iii) cyanoacetic acid, piperidine, $CH_3CN$.

As shown in Scheme 1, 7-bromo-9H-fluoren-2-ylamine is reacted with 1-iodobutane to form (7-bromo-9H-fluoren-2-yl)-dibutyl amine (11). Then, (7-bromo-9H-fluoren-2-yl)-dibutyl amine (11) is reacted with 5-formyl-2-thiopheneboronic acid by Suzuki coupling reaction to obtain 5-(7-dibutylamino-9H-fluoren-2-yl)-thiophene-2-carbaldehyde (12a). Finally, in acetonitrile, 5-(7-dibutylamino-9H-fluoren-2-yl)-thiophene-2-carbaldehyde (12a) is reacted with cyanoacetic acid by using piperidine as a catalyst, to obtain 2-cyano-3-[5-(7-dibutylamino-9H-fluoren-2-yl)-thiophen-2-yl]-acrylic acid (13a).

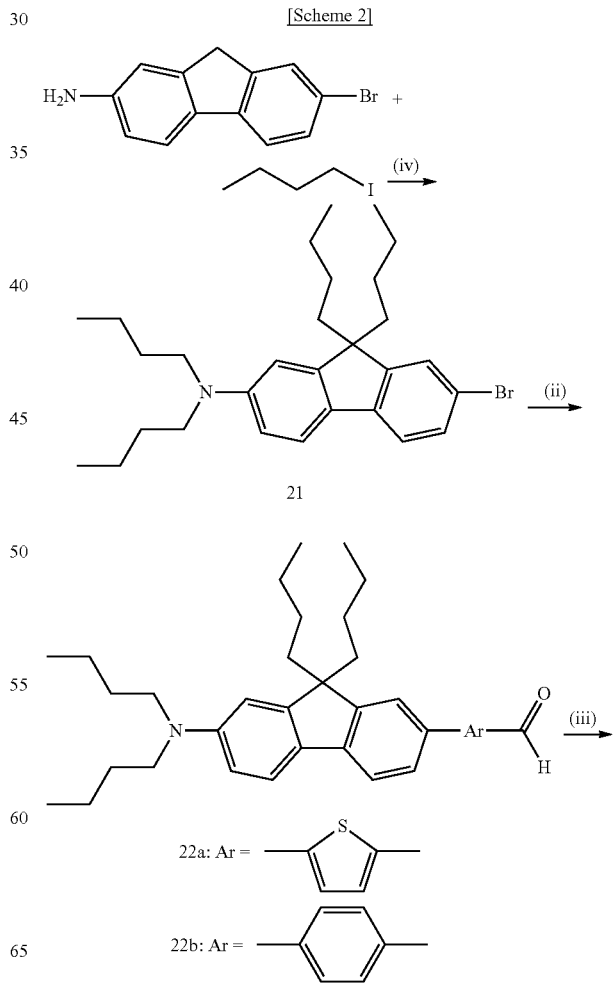

-continued

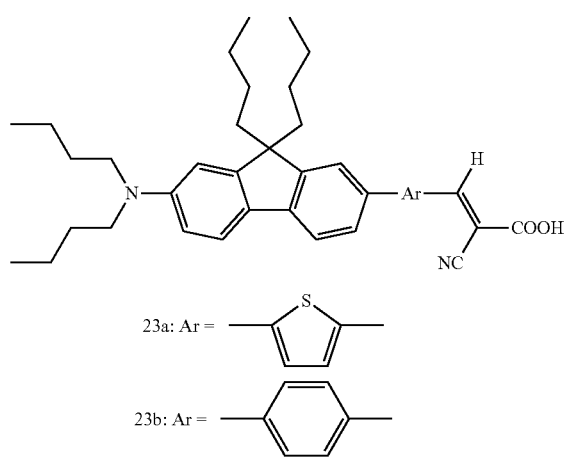

23a: Ar = [thiophene]

23b: Ar = [phenyl]

(ii) PdCl$_2$(dppf), 5-formyl-2-thiopheneboronic acid or 4-formylphenylboronic acid, K$_2$CO$_3$, CH$_3$OH/toluene.
(iii) cyanoacetic acid, piperidine, CH$_3$CN.
(iv) KO$^t$Bu/K$_2$CO$_3$, 1,4-dioxane/DMF.

As shown in Scheme 2, 7-bromo-9H-fluoren-2-ylamine is reacted with 1-iodobutane to form (7-bromo-9,9-dibutyl-9H-fluoren-2-yl)-dibutylamine (21). Then, (7-bromo-9,9-dibutyl-9H-fluoren-2-yl)-dibutylamine (21) is reacted with 5-formyl-2-thiopheneboronic acid by Suzuki coupling reaction to obtain 5-(9,9-Dibutyl-7-dibutylamino-9H-fluoren-2-yl)-thiophene-2-carbaldehyde (22a). Finally, in acetonitrile, 5-(9,9-Dibutyl-7-dibutylamino-9H-fluoren-2-yl)-thiophene-2-carbaldehyde (22a) is reacted with cyanoacetic acid by using piperidine as a catalyst, to obtain 2-Cyano-3-[5-(9,9-dibutyl-7-dibutylamino-9H-fluoren-2-yl)-thiophen-2-yl]-acrylic acid (23a).

[Scheme 3]

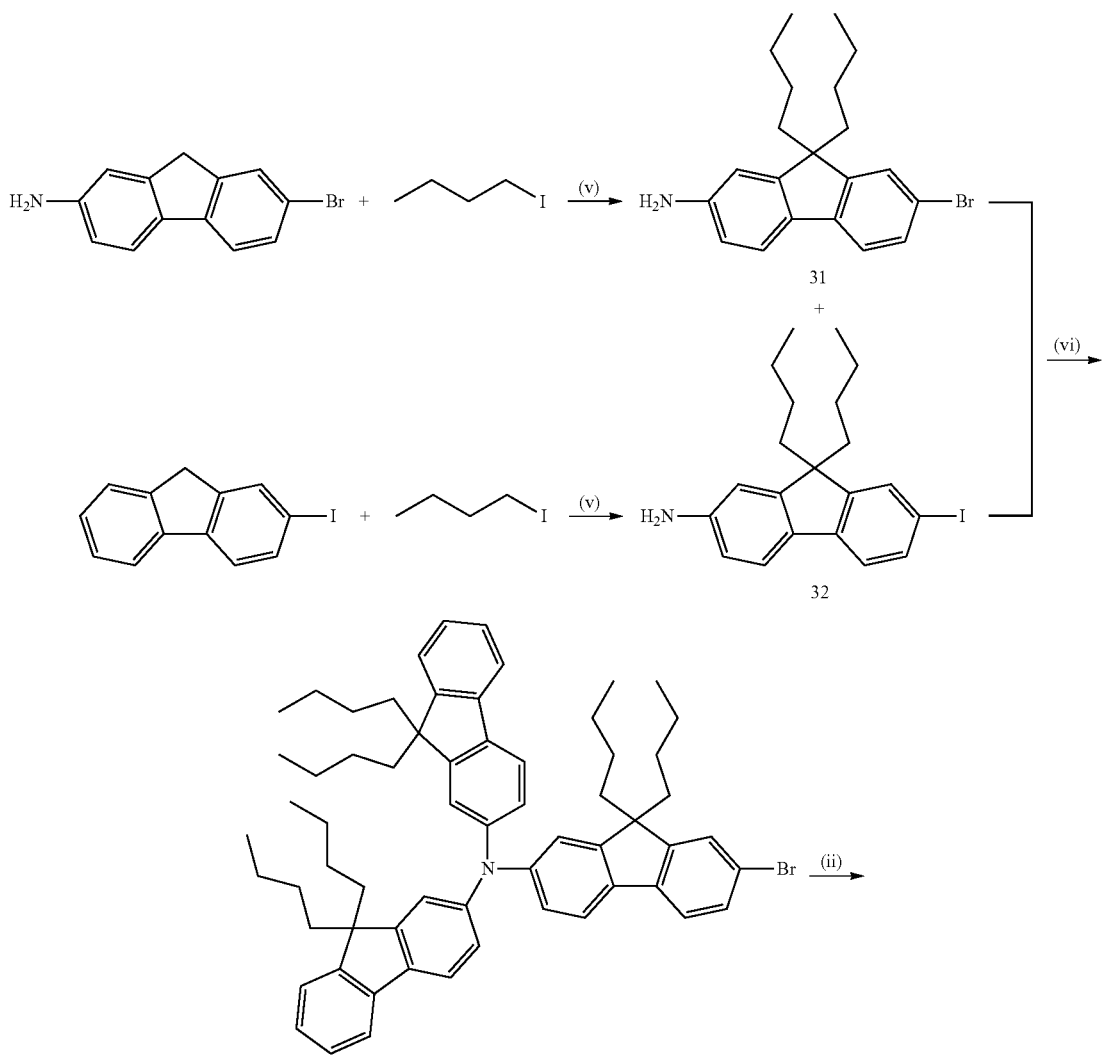

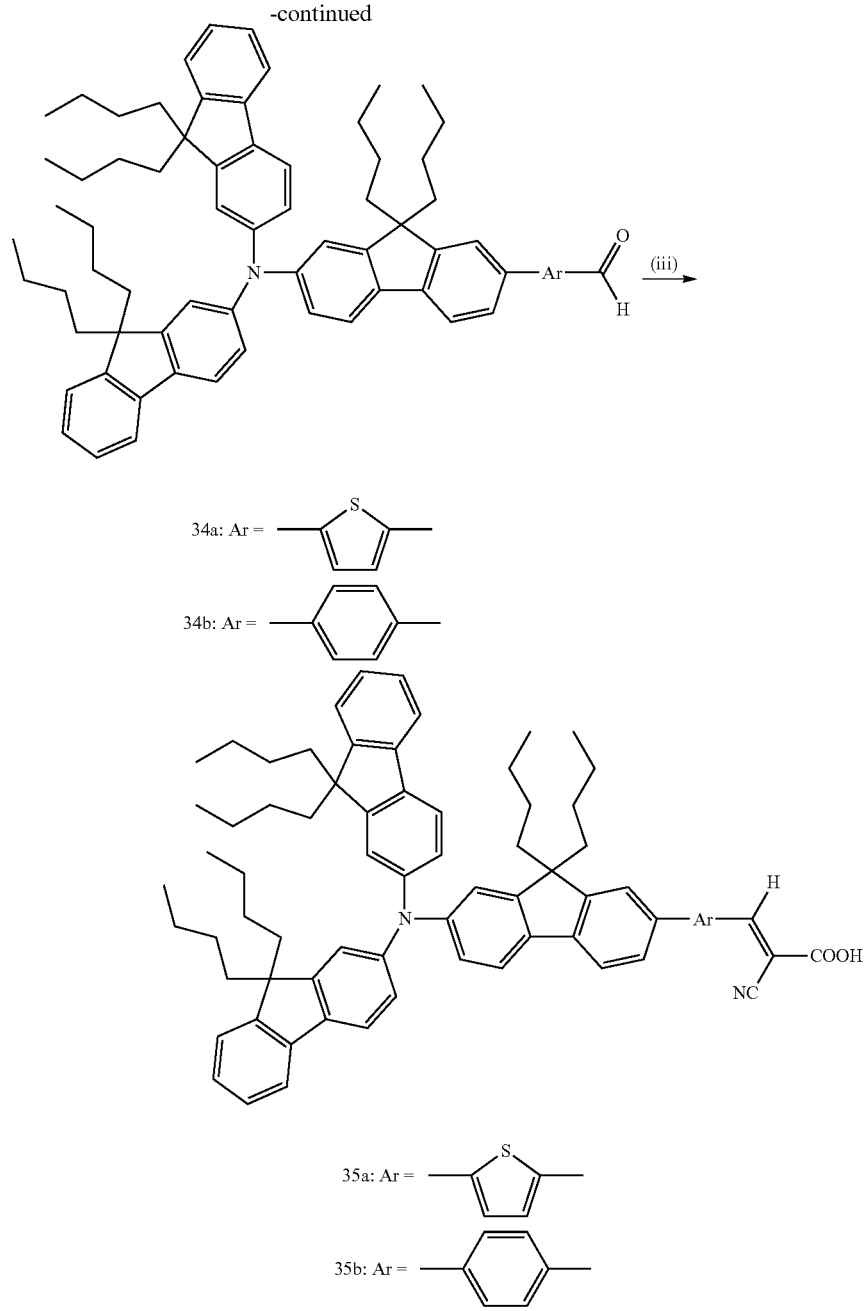

(ii) PdCl$_2$(dppf), 5-formyl-2-thiopheneboronic acid or 4-formylphenylboronic acid, K$_2$CO$_3$, CH$_3$OH/toluene.
(iii) cyanoacetic acid, piperdine, CH$_3$CN.
(v) KO$^t$Bu, THF.
(vi) CuCl, 1,10-phenanthroline, KOH, toluene.

As shown in Scheme 3, 7-bromo-9H-fluoren-2-ylamine is reacted with 1-iodobutane to form 7-bromo-9,9-dibutyl-9H-fluoren-2-ylamine (31); and 2-Iodo-9H-fluorene is reacted with 1-iodobutane to form 9,9-dibutyl-2-iodo-9H-fluorene (32). Then, 7-bromo-9,9-dibutyl-9H-fluoren-2-ylamine (31) is reacted with 9,9-dibutyl-2-iodo-9H-fluorene (32) by Ullman coupling reaction to obtain (7-bromo-9,9-dibutyl-9H-fluoren-2-yl)-bis-(9,9-dibutyl-9H-fluoren-2-yl)amine (33). Next, (7-bromo-9,9-dibutyl-9H-fluoren-2-yl)-bis-(9,9-dibutyl-9H-fluoren-2-yl)amine (33) is reacted with 5-formyl-2-thiopheneboronic acid by Suzuki coupling reaction to obtain 5-{7-[bis-(9,9-dibutyl-9H-fluoren-2-yl)amino]-9,9-dibutyl-9H-fluoren-2-yl}-thiophene-2-carbaldehyde (34a). Finally, in acetonitrile, 5-{7-[bis-(9,9-dibutyl-9H-fluoren-2-yl)amino]-9,9-dibutyl-9H-fluoren-2-yl}-thiophene-2-carbaldehyde (34a) is reacted with cyanoacetic acid by using piperidine as a catalyst, to obtain 3-(5-{7-[bis-(9,9-dibutyl-9H-fluoren-2-yl)amino]-9,9-dibutyl-9H-fluoren-2-yl}-thiophen-2-yl)-2-cyano-acrylic acid (35a).

The method for manufacturing the dye-sensitized solar cell of the present invention is not particularly limited, and the dye-sensitized solar cell of the present invention can be manufacture by the known methods in the art.

The material of the transparent substrate is not particularly limited, as long as the material of the substrate is a transparent material. Preferably, the material of the transparent substrate is a transparent material with good moisture resistance, solvent resistance and weather resistance. Thus, the dye-sensitized solar cell can resist moisture or gas from outsides by the transparent substrate. The specific examples of the transparent substrate include, but are not limited to, transparent inorganic substrates, such as quartz and glass; transparent plastic substrates, such as poly(ethylene terephthalate) (PET), poly (ethylene 2,6-naphthalate) (PEN), polycarbonate (PC), polyethylene (PE), polypropylene (PP), and polyimide (PI). Additionally, the thickness of the transparent substrate is not particularly limited, and can be modified according to the transmittance and the demands for the properties of the dye-sensitized solar cell. In a specific embodiment, the material of the transparent substrate is a glass substrate.

Furthermore, the material of the transparent conductive layer can be indium tin oxide (ITO), fluorine-doped tin oxide (FTO), $ZnO-Ga_2O_3$, $ZnO-Al_2O_3$, or tin-based oxides. In a specific embodiment, fluorine-doped tin oxide is used for the transparent conductive layer.

In addition, the porous semiconductive layer is made of semiconductor particles. Suitable semiconductor particles may include Si, $TiO_2$, $SnO_2$, ZnO, $WO_3$, $Nb_2O_5$, $TiSrO_3$, and the combination thereof. First, the semiconductor particles are prepared in a form of paste, and then the paste is coated on the transparent conductive substrate. The coating method used herein can be blade coating, spin coating, spry coating, or wetting coating. Additionally, the coating can be held for one time or many times, in order to obtain a porous semiconductive layer with suitable thickness. The semiconductive layer can be a single layer or multiple layers, wherein each layer of the multiple layers is formed by semiconductor particles with different diameters. For example, the semiconductor particles with diameters of 5 to 50 nm is coated in a thickness of 5 to 20 μm, and then the semiconductor particles with diameters of 200 to 400 nm is coated in a thickness of 3 to 5 μm thereon. After drying the coated substrate under 50-100° C., the coated substrate is sintered under 400-500° C. for 30 min to obtain a multilayer semicondictive layer.

The dye compound can be dissolved in a suitable solvent to prepare a dye solution. Suitable solvents include, but are not limited to, acetonitrile, methanol, ethanol, propanol, butanol, dimethyl formamide, N-methyl-2-pyrrolidinone, and the combination thereof. Herein, the transparent substrate coated with the semiconductive layer is dipped into a dye solution to make the semiconductive layer absorb the dye in the dye solution completely. After the dye absorption is completed, the transparent substrate coated with the semiconductive layer is taken out and dried. Finally, a photoanode for a dye-sensitized solar cell is obtained.

Besides, the material of the cathode for the dye-sensitized solar cell is not particularly limited, and may include any material with conductivity. Otherwise, the material of the cathode can be an insulating material, as long as there is a conductive layer formed on the surface of the cathode, wherein the surface of the cathode is faced to the photoanode. The material of the cathode can be a material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes. In addition, the liquid electrolyte can be a solution of acetonitrile containing iodine, a solution of N-methyl-2-pyrrolidinone containing iodine, or a solution of 3-methoxy propionitrile containing iodine. In a specific embodiment, the liquid electrolyte can be a solution of acetonitrile containing iodine.

One specific method for manufacturing the dye-sensitized solar cell of the present invention is presented as follow.

First, a paste containing $TiO_2$ particles with diameter of 20~30 nm is coated on a glass substrate covered with fluorine-doped tin oxide (FTO) for one time or several times. Then, the coated glass substrate is sintered under 450° C. for 30 min.

The dye compound is dissolved in a mixture of acetonitrile and t-butanol (1:1 v/v) to formulate a dye solution. Then, the aforementioned glass substrate with porous $TiO_2$ layer is dipped into the dye solution. After the porous $TiO_2$ layer absorbs the dye in the dye solution completely, the resulted glass substrate is taken out and dried. Finally, a photoanode is obtained.

A glass substrate covered with fluorine-doped tin oxide is drilled to form an inlet with a diameter of 0.75 mm, wherein the inlet is used for injecting the electrolyte. Then, a solution of $H_2PtCl_6$ is coated on the glass substrate covered with fluorine-doped tin oxide, and the glass substrate is heated to 400° C. for 15 min to obtain a cathode.

Sequentially, a thermoplastic polymer layer with a thickness of 60 is disposed between the photoanode and the cathode. These two electrodes are pressed under 120 to 140° C. to adhere with each other.

Then, an electrolyte is injected, wherein the electrolyte is a solution of acetonitrile containing 0.03 M $I_2$/0.3 M LiI/0.5 M t-butyl-pyridine. After the inlet is sealed with thermoplastic polymer layer, a dye-sensitized solar cell of the present invention is obtained.

The following examples are intended for the purpose of illustration of the present invention. However, the scope of the present invention should be defined as the claims appended hereto, and the following examples should not be construed as in any way limiting the scope of the present invention. Herein, the molecule of the dye compound is presented in form of free acid. However, the actual form of the dye compound of the present invention may be salt, and more likely, may be alkaline metal salt or quaternary ammonium salt. Without specific explanations, the unit of the parts and percentages used in the examples is calculated by weight, and the temperature is represented by Celsius degrees (° C.). The relation between the parts by weight and the parts by volume is just like the relation between kilogram and liter.

Then, the method for preparing the dye compound of the present invention will be explained with referring to Schemes 1-3.

Example 1

Synthesis of (7-bromo-9H-fluoren-2-yl)-dibutylamine (11)

Under $N_2$ atmosphere, 0.52 parts of 7-bromo-9H-fluoren-2-ylamine, 1.47 parts of 1-iodobutane, and 1.38 parts of potassium carbonate were added into 15 parts of dry dimethylformamide, followed by stirring and mixing. Then, the reaction mixture was heated to 120° C. and reacted for 24 hours. After the reaction mixture was cooled, poured the water into the reaction mixture for quenching the reaction, and using the diethyl ether to extract the product, and magnesium sulfate was used for dehydration. After removing the solvent, the residual was purified with column chromatography method by using dichloromethane/hexane co-solvent as an eluent, to obtain a compound (11) of the present example. This compound was in a form of a yellowish-brown solid, and the yield of this compound was 85%.

Example 2

Synthesis of 5-(7-dibutylamino-9H-fluoren-2-yl)-thiophene-2-carbaldehyde (12a)

Under $N_2$ atmosphere, 0.37 parts of (7-bromo-9H-fluoren-2-yl)-dibutyl amine (11), 0.19 parts of 5-formyl-2-thiopheneboronic acid, 0.41 parts of potassium carbonate, and 0.16 parts of $PdCl_2$(dppf) were added into 5 parts of toluene and 5 parts of $CH_3OH$, followed by stirring and mixing. Then, the reaction mixture was heated to 60° C. and reacted for 18 hours. After the reaction mixture was quenched by water, using the diethyl ether to extract the product, and magnesium sulfate was used for dehydration. After removing the solvent, the residual was purified with chromatography method column by using dichloromethane/hexane co-solvent as an eluent, to obtain a compound (12a) of the present example. This compound was in a form of a tangerine solid, and the yield of this compound was 61%.

Example 3

Synthesis of 4-(7-dibutylamino-9H-fluoren-2-yl)-benzaldehyde (12b)

The process for preparing the dye compound of the present example is the same as that described in Example 2, except that 5-formyl-2-thiopheneboronic acid is substituted with 0.18 parts of 4-formylphenylboronic acid, to obtain a compound (12b) of the present example. This compound was in a form of yellow solid, and the yield of this compound was 53%.

Example 4

Synthesis of 2-cyano-3-[5-(7-dibutylamino-9H-fluoren-2-yl)-thiophen-2-yl]-acrylic acid (13a)

Under $N_2$ atmosphere, 0.18 parts of 5-(7-dibutylamino-9H-fluoren-2-yl)-thiophene-2-carbaldehyde (12a), 0.05 parts of cyanoacetic acid, and 0.017 parts of piperidine were added into acetonitrile, followed by stirring and mixing. Then, the reaction mixture was heated to 90° C. and reacted for 6 hours. After the reaction mixture was cooled to room temperature, the reaction mixture was filtrated to obtain a solid. Then, the solid was washed with water, ether, and acetonitrile sequentially to obtain a dark red solid. Finally, this crude was purified with column chromatography method by using dichloromethane/methanol co-solvent as an eluent, to obtain a compound (13a) of the present example. This compound was in a form of a dark red solid, and the yield of this compound was 73%.

Example 5

Synthesis of 2-cyano-3-[4-(7-dibutylamino-9H-fluoren-2-yl)-phenyl]-acrylic acid (13b)

The process for preparing the dye compound of the present example is the same as that described in Example 4, except that 5-(7-dibutylamino-9H-fluoren-2-yl)-thiophene-2-carbaldehyde (12a) is substituted with 0.18 parts of 4-(7-dibutylamino-9H-fluoren-2-yl)-benzaldehyde (12b), to obtain a compound (13b) of the present example. This compound was in a form of dark red solid, and the yield of this compound was 78%.

Example 6

Synthesis of (7-bromo-9,9-dibutyl-9H-fluoren-2-yl)-dibutylamine (21)

Under $N_2$ atmosphere, 0.52 parts of 7-bromo-9H-fluoren-2-ylamine, 2.21 parts of 1-iodobutane, 0.67 parts of potassium tert-butoxide, and 0.83 parts of potassium carbonate were added into 10 parts of dry dimethylformamide and 10 parts of 1,4-dioxane, followed by stirring and mixing. Then, the reaction mixture was heated to 95° C. and reacted for 24 hours. After the reaction mixture was cooled, poured the water into the reaction mixture for quenching the reaction, using the diethyl ether to extract the product, and magnesium sulfate was used for dehydration. After removing the solvent, the residual was purified with column chromatography method by using dichloromethane/hexane co-solvent as an eluent, to obtain a compound (21) of the present example. This compound was in a form of a light yellow solid, and the yield of this compound was 83%.

Example 7

Synthesis of 5-(9,9-dibutyl-7-dibutylamino-9H-fluoren-2-yl)-thiophene-2-carbaldehyde (22a)

The process for preparing the dye compound of the present example is the same as that described in Example 2, except that (7-bromo-9H-fluoren-2-yl)-dibutylamine (11) is substituted with 0.49 parts of (7-bromo-9,9-dibutyl-9H-fluoren-2-yl)-dibutylamine (21), to obtain a compound (22a) of the present example. This compound was in a form of a tangerine solid, and the yield of this compound was 52%.

Example 8

Synthesis of 4-(9,9-dibutyl-7-dibutylamino-9H-fluoren-2-yl)-benzaldehyde (22b)

The process for preparing the dye compound of the present example is the same as that described in Example 7, except that 5-formyl-2-thiopheneboronic acid is substituted with 0.18 parts of 4-formylphenylboronic acid, to obtain a compound (22b) of the present example. This compound was in a form of a yellow solid, and the yield of this compound was 61%.

Example 9

Synthesis of 2-cyano-3-[5-(9,9-dibutyl-7-dibutylamino-9H-fluoren-2-yl)-thiophen-2-yl]-acrylic acid (23a)

The process for preparing the dye compound of the present example is the same as that described in Example 4, except that 5-(7-dibutylamino-9H-fluoren-2-yl)-thiophene-2-carbaldehyde (12a) is substituted with 0.23 parts of 5-(9,9-dibutyl-7-dibutylamino-9H-fluoren-2-yl)-thiophene-2-carbaldehyde (22a), to obtain a compound (23a) of the present example. This compound was in a form of a red solid, and the yield of this compound was 86%.

Example 10

Synthesis of 2-cyano-3-[4-(9,9-dibutyl-7-dibutylamino-9H-fluoren-2-yl)-phenyl]-acrylic acid (23b)

The process for preparing the dye compound of the present example is the same as that described in Example 9, except that 5-(9,9-dibutyl-7-dibutylamino-9H-fluoren-2-yl)-thiophene-2-carbaldehyde (22a) is substituted with 0.23 parts of 4-(9,9-dibutyl-7-dibutylamino-9H-fluoren-2-yl)-benzaldehyde (22b), to obtain a compound (23b) of the present example. This compound was in a form of a tangerine solid, and the yield of this compound was 68%.

Example 11

Synthesis of 7-bromo-9,9-dibutyl-9H-fluoren-2-ylamine (31)

Under $N_2$ atmosphere, 0.52 parts of 7-bromo-9H-fluoren-2-ylamine, 2.21 parts of 1-iodobutane, and 1.35 parts of potassium tert-butoxide were added into 20 parts of dry tetrahydrofuran, followed by stirring and mixing. Then, the reaction mixture was heated to 50° C. and reacted for 18 hours. After the reaction mixture was cooled, water was used for quenching the reaction, diethyl ether was used for extracting the product, and magnesium sulfate was used for dehydration. After removing the solvent, the residual was purified with column chromatography method by using dichloromethane/hexane co-solvent as an eluent, to obtain a compound (31) of the present example. This compound was in a form of a brown-yellow solid, and the yield of this compound was 79%.

Example 12

Synthesis of 9,9-dibutyl-2-iodo-9H-fluorene (32)

Under $N_2$ atmosphere, 0.58 parts of 2-iodo-9H-fluorene, 1.10 parts of 1-iodobutane, and 0.67 parts of potassium tert-butoxide were added into 15 parts of dry tetrahydrofuran, followed by stirring and mixing. Then, the reaction mixture was heated to 50° C. and reacted for 12 hours. After the reaction mixture was cooled, poured the water into the reaction mixture for quenching the reaction, using the diethyl ether to extract the product, and magnesium sulfate was used for dehydration. After removing the solvent, the residual was purified with column chromatography method by using hexane as an eluent, to obtain a compound (32) of the present example. This compound was in a form of a light yellow solid, and the yield of this compound was 94%.

Example 13

Synthesis of (7-bromo-9,9-dibutyl-9H-fluoren-2-yl)-bis-(9,9-dibutyl-9H-fluoren-2-yl)amine (33)

Under $N_2$ atmosphere, 0.37 parts of 7-bromo-9,9-dibutyl-9H-fluoren-2-ylamine (31), 0.89 parts of 9,9-dibutyl-2-iodo-9H-fluorene (32), 0.17 parts of potassium hydroxide, 0.11 parts of 1,10-phenanthroline, and 0.03 parts of cuprous chloride were added into 10 parts of toluene, followed by stirring and mixing. Then, the reaction mixture was heated to 120° C. and reacted under reflux for 24 hours. After the reaction was quenched by water, diethyl ether was used for extracting the product, and magnesium sulfate was used for dehydration. After removing the solvent, the residual was purified with column chromatography method by using dichloromethane/hexane co-solvent as an eluent, to obtain a compound (33) of the present example. This compound was in a form of a tangerine solid, and the yield of this compound was 57%.

Example 14

Synthesis of 5-{7-[bis-(9,9-dibutyl-9H-fluoren-2-yl)amino]-9,9-dibutyl-9H-fluoren-2-yl}-thiophene-2-carbaldehyde (34a)

The process for preparing the dye compound of the present example is the same as that described in Example 2, except that (7-bromo-9H-fluoren-2-yl)-dibutylamine (11) is substituted with 0.92 parts of (7-bromo-9,9-dibutyl-9H-fluoren-2-yl)-bis-(9,9-dibutyl-9H-fluoren-2-yl) amine (33), to obtain a compound (34a) of the present example. This compound was in a form of a tangerine solid, and the yield of this compound was 38%.

Example 15

Synthesis of 4-{7-[bis-(9,9-dibutyl-9H-fluoren-2-yl)-amino]-9,9-dibutyl-9H-fluoren-2-yl}-benzaldehyde (34b)

The process for preparing the dye compound of the present example is the same as that described in Example 14, except that 5-formyl-2-thiopheneboronic acid is substituted with 0.18 parts of 4-formylphenylboronic acid, to obtain a compound (34b) of the present example. This compound was in a form of a yellow solid, and the yield of this compound was 48%.

Example 16

Synthesis of 3-(5-{7-[Bis-(9,9-dibutyl-9H-fluoren-2-yl)amino]-9,9-dibutyl-9H-fluoren-2-yl}-thiophen-2-yl)-2-cyano-acrylic acid (35a)

The process for preparing the dye compound of the present example is the same as that described in Example 4, except that 5-(7-dibutylamino-9H-fluoren-2-yl)-thiophene-2-carbaldehyde (12a) is substituted with 0.41 parts of 5-{7-[bis-(9,9-dibutyl-9H-fluoren-2-yl) amino]-9,9-dibutyl-9H-fluoren-2-yl}-thiophene-2-carbaldehyde (34a), to obtain a compound (35a) of the present example. This compound was in a form of a tangerine solid, and the yield of this compound was 51%.

Example 17

Synthesis of 3-(4-{7-[Bis-(9,9-dibutyl-9H-fluoren-2-yl)amino]-9,9-dibutyl-9H-fluoren-2-yl}-phenyl)-2-cyano-acrylic acid (35b)

The process for preparing the dye compound of the present example is the same as that described in Example 16, except that 5-{7-[bis-(9,9-dibutyl-9H-fluoren-2-yl)amino]-9,9-dibutyl-9H-fluoren-2-yl}-thiophe ne-2-carbaldehyde (34a) is substituted with 0.42 parts of 4-{7-[bis-(9,9-dibutyl-9H-fluoren-2-yl)-amino]-9,9-dibutyl-9H-fluoren-2-yl}-benzal dehyde (34b), to obtain a compound (35b) of the present example. This compound was in a form of a tangerine solid, and the yield of this compound was 65%.

Example 18

Preparation of a Dye-Sensitized Solar Cell

A paste containing $TiO_2$ particles with diameter of 20~30 nm was coated on a glass substrate covered with fluorine-doped tin oxide (PTO) for one time or several times, wherein the thickness of the glass substrate was 4 mm and the electric resistance of the glass substrate is 10Ω/□. Then, the coated glass substrate was sintered under 450° C. for 30 min, and the thickness of the sintered porous $TiO_2$ layer was 10 to 12 μm.

The dye compound prepared by Example 4 was dissolved in a mixture of acetonitrile and t-butanol (1:1 v/v) to prepare a dye solution containing 0.5 mM dye compound. Then, the aforementioned glass substrate covered with porous $TiO_2$ layer was dipped into the dye solution to make the dye adhere on the porous $TiO_2$ layer. After 16 to 24 hours, the resulted glass substrate was taken out and dried, and then a photoanode was obtained.

A glass substrate covered with fluorine-doped tin oxide was drilled to form an inlet with a diameter of 0.75 mm, wherein the inlet was used for injecting the electrolyte. Then, a solution of $H_2PtCl_6$ (2 mg Pt in 1 ml ethanol) was coated on the glass substrate covered with fluorine-doped tin oxide, and the resulted glass substrate was heated to 400° C. for 15 min to obtain a cathode.

Sequentially, a thermoplastic polymer layer with a thickness of 60 μm was disposed between the photoanode and the cathode. These two electrodes were pressed under 120 to 140° C. to adhere with each other.

Then, an electrolyte was injected, wherein the electrolyte was a solution of acetonitrile containing 0.03 M $I_2$/0.3 M LiI/0.5 M t-butyl-pyridine. After the inlet was sealed with thermoplastic polymer layer, a dye-sensitized solar cell of the present example was obtained.

Example 19

Preparation of a Dye-Sensitized Solar Cell

The process for preparing the dye-sensitized solar cell of the present example is the same as that described in Example 18, except that the dye compound prepared in Example 4 is substituted with the dye compound prepared in Example 5.

Example 20

Preparation of a Dye-Sensitized Solar Cell

The process for preparing the dye-sensitized solar cell of the present example is the same as that described in Example 18, except that the dye compound prepared in Example 4 is substituted with the dye compound prepared in Example 9.

Example 21

Preparation of a Dye-Sensitized Solar Cell

The process for preparing the dye-sensitized solar cell of the present example is the same as that described in Example 18, except that the dye compound prepared in Example 4 is substituted with the dye compound prepared in Example 10.

Example 22

Preparation of a Dye-Sensitized Solar Cell

The process for preparing the dye-sensitized solar cell of the present example is the same as that described in Example 18, except that the dye compound prepared in Example 4 is substituted with the dye compound prepared in Example 16.

Example 23

Preparation of a Dye-Sensitized Solar Cell

The process for preparing the dye-sensitized solar cell of the present example is the same as that described in Example 18, except that the dye compound prepared in Example 4 is substituted with the dye compound prepared in Example 17.

Testing Methods and Results

UV-Vis Spectrum

Dimethyl formamide was used as a solvent to prepare dye solutions containing $1.0 \times 10^{-5}$ M of the dye compounds prepared in Example 4, Example 5, Example 9, Example 10, Example 16, and Example 17. Then, the UV-Vis spectrum of each dye solution was measured.

Test for the Photoelectric Characteristics

The short circuit current ($J_{SC}$), open circuit voltage ($V_{OC}$), filling factor (FF), photoelectric conversion efficiency (η), and incident photon-to-current conversion efficiency (IPCE) of the dye-sensitized solar cells prepared by Examples 18-23 were measured under the illumination of AM 1.5 stimulated light. The testing results are shown in the following Table 1:

TABLE 1

Testing results of the dye and the dye-sensitized solar cell

| Dye | | Molar absorption coefficient at the wavelength of the maximum absorption ($M^{-1}cm^{-1}$)/$\lambda_{max}$ (nm) | $J_{SC}$ (mA/cm$^2$) | $V_{OC}$ (V) | FF | η (%) |
|---|---|---|---|---|---|---|
| Example 18 | 13a | 25200/421 | 6.28 | 0.61 | 0.66 | 2.54 |
| Example 19 | 13b | 23200/384 | 8.40 | 0.60 | 0.63 | 3.15 |
| Example 20 | 23a | 66200/427 | 13.16 | 0.69 | 0.64 | 5.82 |
| Example 21 | 23b | 73100/386 | 11.00 | 0.68 | 0.58 | 4.68 |
| Example 22 | 35a | 66800/421 | 10.28 | 0.69 | 0.65 | 4.90 |
| Example 23 | 35b | 35200/380 | 10.30 | 0.70 | 0.63 | 4.58 |

According to the results shown in Table 1, the dye compounds of the present invention have high molar absorption coefficient. Hence, the dye-sensitized solar cell using the dye compound of the present invention has good photoelectric conversion efficiency.

In conclusion, the present invention is different from the prior arts in several ways, such as in purposes, methods and efficiency, or even in technology and research and design. Although the present invention has been explained in relation to its preferred embodiment, it is to be understood that many other possible modifications and variations can be made without departing from the scope of the invention as hereinafter claimed. Hence, the scope of the present invention should be defined as the claims appended hereto, and the foregoing examples should not be construed as in any way limiting the scope of the present invention.

What is claimed is:

1. A dye compound represented by the following formula (I), or a salt thereof:

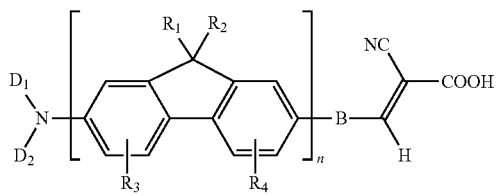

wherein, $R_1, R_2, R_3$, and $R_4$ are each independently H, $C_1\sim C_{12}$ alkyl, $C_1\sim C_{12}$ alkoxy, or a halogen, and n is 1, 2, or 3;

$D_1$, and $D_2$ are each independently $C_1\sim C_{12}$ alkyl,

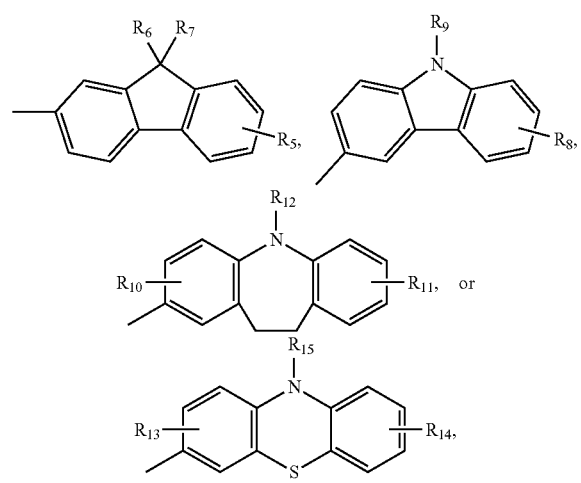

or $D_1$, $D_2$, and N bond together to form

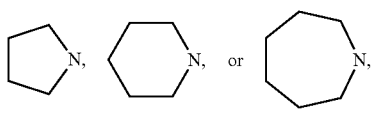

wherein $R_5, R_6, R_7, R_8, R_{10}, R_{11}, R_{13}$, and $R_{14}$ are each independently H, $C_1\sim C_{12}$ alkyl, $C_1\sim C_{12}$ alkoxy, amino, or halogen, and $R_9, R_{12}$, and $R_{15}$ are each independently H, or $C_1\sim C_{12}$ alkyl;

B is

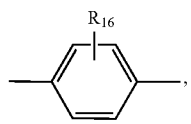

wherein
$R_{16}$ is H, $C_1\sim C_{12}$ alkyl, $C_1\sim C_{12}$ alkoxy, or halogen.

2. The dye compound as claimed in claim 1, wherein n is 1.

3. The dye compound as claimed in claim 1, wherein $D_1$, and $D_2$ are each independently $C_1\sim C_{12}$ alkyl,

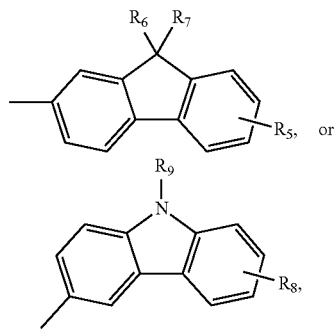

wherein $R_5, R_6, R_7$, and $R_8$ are each independently H, $C_1\sim C_{12}$ alkyl, $C_1\sim C_{12}$ alkoxy, amino, or halogen, and $R_9$ is H, or $C_1\sim C_{12}$ alkyl.

4. The dye compound as claimed in claim 1, wherein $R_1, R_2, R_3, R_4, R_5, R_6, R_7, R_8$, and $R_{16}$ are each independently H, $C_1\sim C_{12}$ alkyl, or $C_1\sim C_{12}$ alkoxy.

5. The dye compound as claimed in claim 4, wherein $R_1, R_2, R_3, R_4, R_5, R_6, R_7, R_8$, and $R_{16}$ are each independently H, or $C_1\sim C_{12}$ alkyl.

6. The dye compound as claimed in claim 1, wherein $D_1$, and $D_2$ are each independently $C_1\sim C_{12}$ alkyl, or

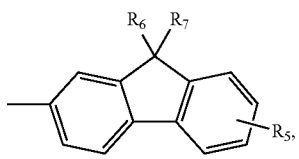

wherein $R_5, R_6$, and $R_7$ are each independently H, $C_1\sim C_{12}$ alkyl, $C_1\sim C_{12}$ alkoxy, amino, or halogen.

7. The dye compound as claimed in claim 6, wherein $R_1, R_2, R_3, R_4, R_5, R_6, R_7$, and $R_{16}$ are each independently H, $C_1\sim C_{12}$ alkyl, $C_1\sim C_{12}$ alkoxy.

8. The dye compound as claimed in claim 7, wherein $R_1, R_2, R_3, R_4, R_5, R_6, R_7$, and $R_{16}$ are each independently H, or $C_1\sim C_{12}$ alkyl.

9. The dye compound as claimed in claim 8, wherein $R_{16}$ is H.

10. The dye compound as claimed in claim 1, wherein the dye compound is a dye compound for a dye-sensitized solar cell.

11. A dye solution, comprising:
(A) a dye compound represented by the following formula (I), or a salt thereof, wherein the content of the dye compound is 0.01-1 wt %:

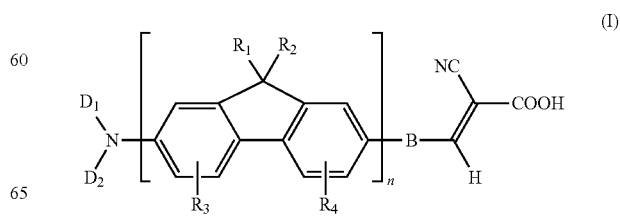

wherein, $R_1$, $R_2$, $R_3$, and $R_4$ are each independently H, $C_1\sim C_{12}$ alkyl, $C_1\sim C_{12}$ alkoxy, or a halogen, and n is 1, 2, or 3;

$D_1$, and $D_2$ are each independently $C_1\sim C_{12}$ alkyl,

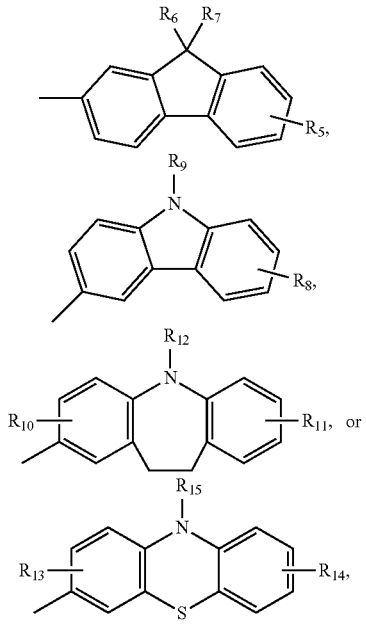

or $D_1$, $D_2$, and N bond together to form

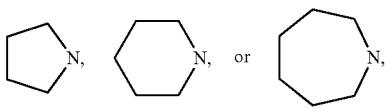

wherein $R_5$, $R_6$, $R_7$, $R_8$, $R_{10}$, $R_{11}$, $R_{13}$, and $R_{14}$ are each independently H, $C_1\sim C_{12}$ alkyl, $C_1\sim C_{12}$ alkoxy, amino, or halogen, and $R_9$, $R_{12}$, and $R_{15}$ are each independently H, or $C_1\sim C_{12}$ alkyl;

B is

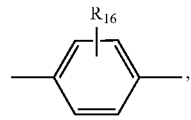

wherein $R_{16}$ is H, $C_1\sim C_{12}$ alkyl, $C_1\sim C_{12}$ alkoxy, or halogen; and (B) an organic solvent, wherein the content of the organic solvent is 99.99-99 wt %, and the organic solvent is selected from the group consisting of acetonitrile, methanol, ethanol, propanol, butanol, dimethyl formamide, and N-methyl-2-pyrrolidinone.

12. The dye compound as claimed in claim 1, wherein the formula (I) is the following formula (13b), (23b), or (35b):

(13b)

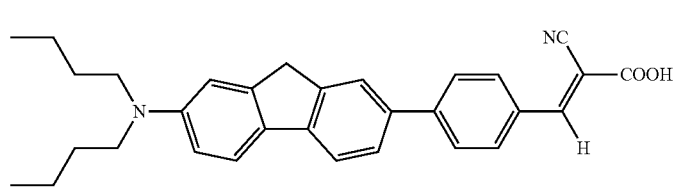

(23b)

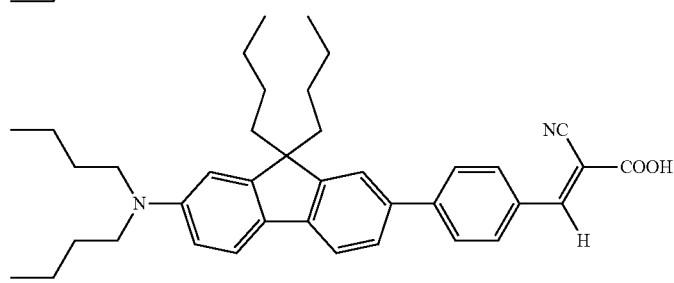

(35b)

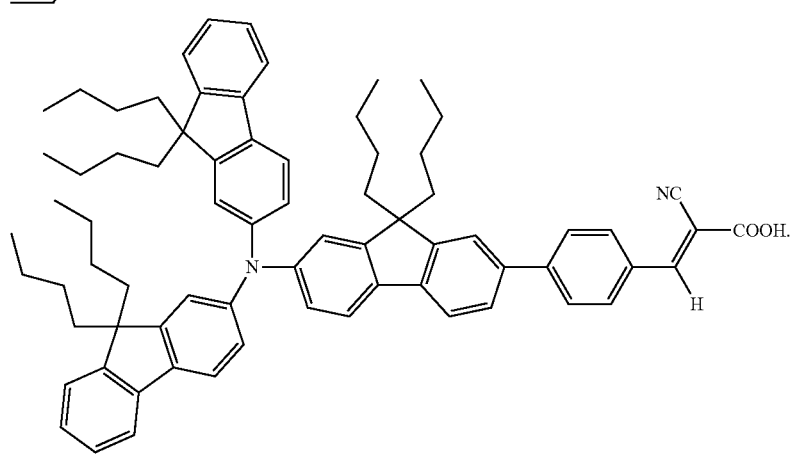

* * * * *